United States Patent
Lee et al.

(10) Patent No.: US 6,576,775 B1
(45) Date of Patent: Jun. 10, 2003

(54) PROCESS FOR PRODUCING SIMVASTATIN

(75) Inventors: Kwang-Hyuk Lee, Sungnam-shi (KR); Jin-Wan Kim, Seoul (KR); Kwang-Do Choi, Ahnyang-shi (KR); Hun Bae, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 10/203,633

(22) PCT Filed: Mar. 30, 2000

(86) PCT No.: PCT/KR00/00283
§ 371 (c)(1),
(2), (4) Date: Aug. 20, 2002

(87) PCT Pub. No.: WO01/72734
PCT Pub. Date: Oct. 4, 2001

(51) Int. Cl.[7] .............................................. C07D 309/10
(52) U.S. Cl. ....................................................... 549/292
(58) Field of Search .......................................... 549/292

(56) References Cited

U.S. PATENT DOCUMENTS 5,393,893 A   2/1995   Kubela et al. ............... 549/292

FOREIGN PATENT DOCUMENTS

EP   0511867 B1   4/1992   ......... C07C/69/732

Primary Examiner—Amelia Owens
(74) Attorney, Agent, or Firm—Jacobson Holman PLLC

(57) ABSTRACT

The present invention relates to a process for producing Simvastatin comprising acylating 6(R)-[2-(8'(S)-hydroxy-2'(S), 6'(R)-dimethyl-1', 2', 6', 7', 8', 8'a(R)-hexahydronaphthyl-1'(S)ethyl-4(R)-t-butyldimethylsilyloxy-3,4,5,6-tetrahydro-2H-pyran-2-on with the carboxylic acid compound of formula (VI):

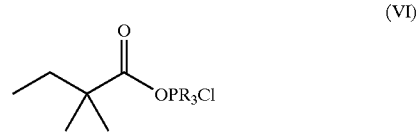

(VI)

wherein R is methyl, ethyl, propyl, n-butyl, t-butyl or phenyl, and hydroxylating the resulting compound.

6 Claims, No Drawings

PROCESS FOR PRODUCING SIMVASTATIN

This is a Nationalization of PCT/KR00/00283, Mar. 30, 2000 and published in the English.

FIELD OF THE INVENTION

The present invention relates to a process for producing Simvastatin compound. This compound has the following formula I:

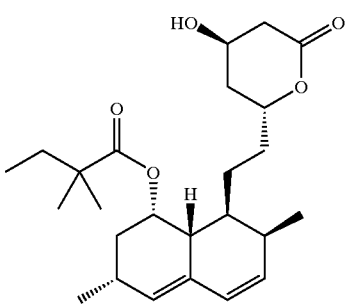

and is useful in inhibiting the biosynthesis of cholesterol.

It is known that Simvastatin compound is a suppressor of HMG CoA reductase and a medicament useful for the treatment of hypercholesterolemia. Several processes for producing said compound are disclosed. One is disclosed in U.S. Pat. No. 4,444,784 (corresponding to Korean Publication Patent No. 85-669) with the following reaction mechanism:

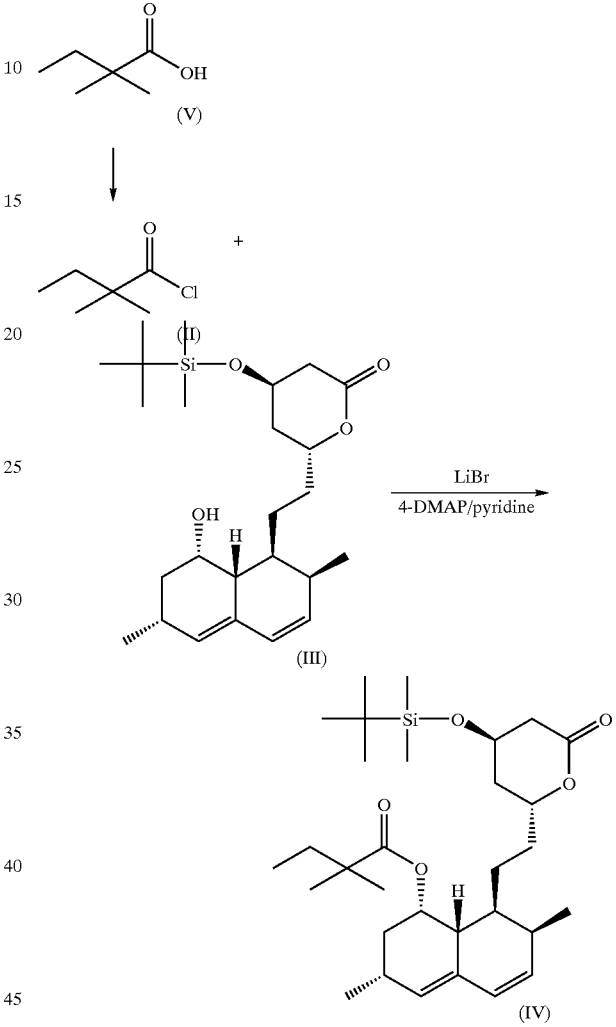

DESCRIPTION OF THE PRIOR ART

The said process described in U.S. Pat. No. 4,444,784 is generally performed in the presence of an excess acylchloride (II) under the condition of high temperature and a long reaction time. In addition, said process has the following disadvantages: i) lower yield of acylated substance; ii) production of by-product due to removal of t-butyldimethylsilyloxy radical; and iii) difficulty of separating the resulting substance, ester (IV), from residual alcohol (III) and acylchloride (II). The residual substances may inhibit the crystallization of the resulting substance.

A process for reforming the above-mentioned process is described in U.S. Pat. No. 4,845,237. Its reaction mechanism is as follows:

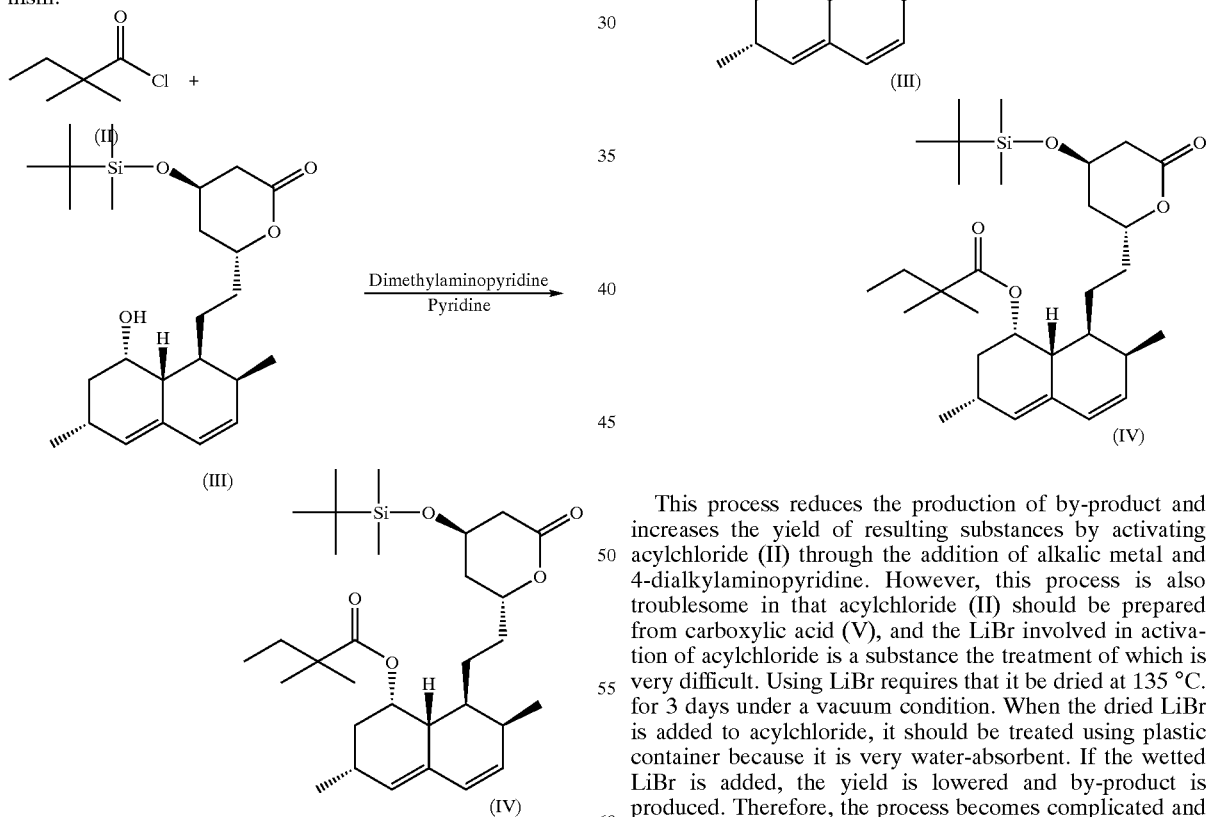

This process reduces the production of by-product and increases the yield of resulting substances by activating acylchloride (II) through the addition of alkalic metal and 4-dialkylaminopyridine. However, this process is also troublesome in that acylchloride (II) should be prepared from carboxylic acid (V), and the LiBr involved in activation of acylchloride is a substance the treatment of which is very difficult. Using LiBr requires that it be dried at 135 °C. for 3 days under a vacuum condition. When the dried LiBr is added to acylchloride, it should be treated using plastic container because it is very water-absorbent. If the wetted LiBr is added, the yield is lowered and by-product is produced. Therefore, the process becomes complicated and difficult.

Accordingly, we have researched and developed a new process, which acylchloride (II), and without the use of LiBr.

DETAILED DESCRIPTION OF THE INVENTION

The present invention provides a process for producing Simvastatin comprising the steps of acylating of 6(R)-[2-(8'

(s)-hydroxy-2'(s), 6'(R)-dimethyl-1', 2', 6', 7', 8', 8'a(R)-hexahydronaphthyl-1'(S) ethyl-4(R)-t-butylmethylsilyloxy-3,4,5,6-tetrahydro-2H-pyran-2-on with carboxylic acid compound (VI), and hydroxylating of acylated compound. The said carboxylic acid compound has the following formula (VI):

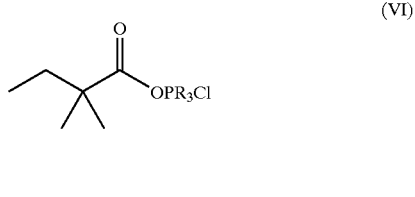

(VI)

wherein, R is methyl, ethyl, propyl, n-butyl, t-butyl, or phenyl.

In the present invention, carboxylic acid (VI) used for acylation is activated by trialkylphosphine and halogen compounds, and is directly used without separation, which allows for the simplification of the process. This reaction mechanism is as follows:

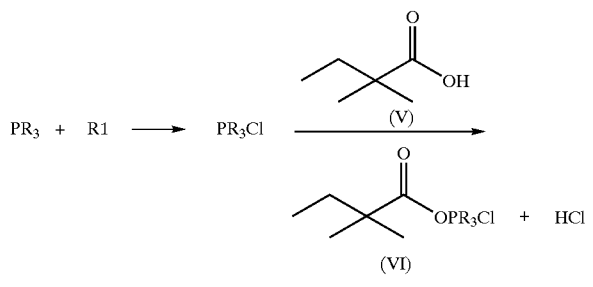

wherein, R is methyl, ethyl, propyl, n-butyl, t-butyl, or phenyl, R1 is a halogen compounds, such as hexachloroethane, carbon tetrachloride, carbon tetrabromide, or hexachloroacetone. When activated carboxylic acid (VI), which is not separated or purified, reacts with alchol (III), a higher yield of acylated substance (IV) is obtained.

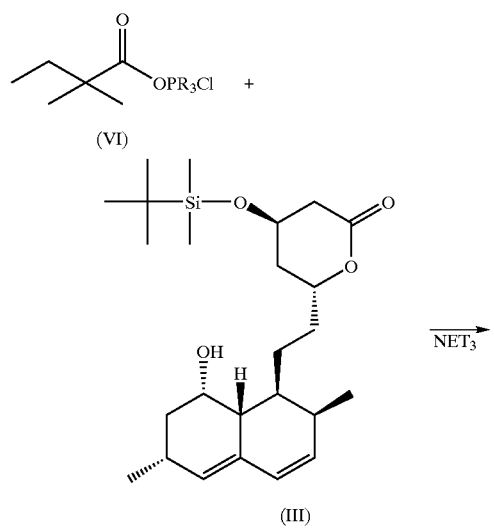

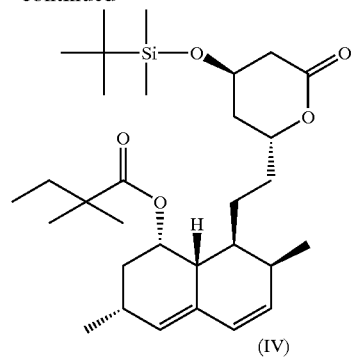

(IV)

The formula (III) compound of the invention is easily prepared by those skilled in the art. It is preferable that $PR_3$ of the initial compound (VI) is triphenylphosphine. The halogen compound is preferably hexachloroethane. It may be used in amount of from 1.0 to 4.0 equivalent, preferably from 3.0 to 3.6 equivalent. Temperature is from 0 °C. to 110 °C., preferably 83° C.

The solvent is used alone or in combination with inert solvents, including acetonitrile, dichioromethane, dichloroethane, cyclohexane, and toluene, most preferably dichioroethane.

It is to be understood that the examples which follow, are intended to illustrate and not limit the scope of the invention.

EXAMPLES

Example 1

6(R)-[2-(8'(S)-(4-Butyl-2,2-dimethyloxy)-2'(S), 6' (R)-Dimethyl-1', 2', 6 ', 7', 8', 8'a(R)-Hexahydronaphthel-1'(S)ethyl-4(R)-t-butyldimethylsilyloxy-3,4,5,6-tetrahydro-2H-pyran-2-on After dissolving 1.8 g of triphenylphosphine into 100 ml of dichloroethane solution, 19.6 g of hexachloroethane was mixed. This solution was stirred at 20 °C. for 1 hr 8.0 g of 2,2-dimethylbutylic acid was added to a solution, and the resulting solution was stirred for 45 min. After stirring, 10 g of 6(R)-[2-(8'(S)-hydroxy-2'(S),6'(R)-dimethyl-1',2',6',7',8', 8'a(R)-hexahydronaphthyl-1'(S)ethlyl-4(R)-t-butyldimethylsilyloxy-3,4,5,6-tetrahydro-2H-pyran-2-on was added to the solution, and this solution was mildly agitated for 20 hr. As a result of monitoring with HPLC, the conversion rate of initial substance is 99% or more, and the content ratio of desirable substance (IV) and by-product, such as unsaturated lactone, was 96–97% and 1–2%, respectively. After the conversion was completed, the solution was cooled to 10 °C., and 100 ml of 2% hydrochloride was mixed. The resulting solution was stirred and the organic layer was separated. The reaction solution was condensed, and triphenyloxide was crystallized by mixing with 100 ml of cyclohexan. The solution containing crystal was cooled to 10° C., stirred for 2 hr, filtered, and then washed with cooled cyclohexan to obtain the title compound.

Example 2

6(R)-[2-(8'(S)-(4-Butyl-2,2-dimethyloxy)-2'(S), 6' (R)-Dimethyl-1', 2', 6', 7', 8', 8'a(R)-Hexahydronaphthyl-1'(S)ethyl4(R)-t-butyldimethylsilyloxy-3,4,5,6-tetrahydro-2H-pyran-2-on After dissolving 18.1 g of triphenylphosphine into 50 ml of dichloroethane solution, 19.6 g of hexachloroethane was mixed. This solution was added dropwise to the solution which 8.0 g of 2,2-dimethylbutylic acid being added to 50 ml of dichloroethane. The resulting solution was stirred for 1 hr. After stirring, 10 g of 6(R)-[2-(8'(S)-hydroxy-2'(S), 6'(R)-dimethyl-1', 2', 6', 7', 8', 8'a(R)-hexahydronaphthyl-1' (S)ethyl-4(R)-t-butyldimethylsilyloxy-3,4,5,6-tetrahydro-2H-pyran-2-on was added to the solution, and this solution was mildly agitated for 20 hr. The solution was cooled to 10 °C., and 100 ml of 2% hydrochloride was mixed. The resulting solution was stirred and the organic layer was separated. The solution was cooled to 10° C., stirred for 2 hr, filtered, and then washed with cooled cyclohexan to obtain the title compound.

Example 3

Production of Simvastatin 120 ml of acetonitrile was added to a concentrated solution of 6(R)-[2-(8'(S)-(4-butyl-2,2-dimethyloxy)-2'(S), 6'(R)-dimethyl-1', 2', 6', 7', 8', 8'a(R)-hexahydronaphthyl-1' (S)ethyl4(R)-t-butyldimethylsilyloxy-3,4,5,6-tetrahydro-2H-pyran-2-on obtained by example 1 or 2. Seven ml of distilled water and 0.5 ml of methanesulfonic acid were added to the solution. This solution was stirred at 50 °C. for 3 hr. After stirring, 42 ml of 2N NaOH was added to the solution, and the resulting solution was stirred. 150 ml of Ethyl acetate and 150 ml of distilled water were added to a solution, stirred, and the aqueous layer was separated. The organic layer was separated by acidifying the aqueous layer mixed with 125 ml of ethyl acetate using hydrochloride, and concentrated. The concentrate was mixed with 150 ml of toluene and mildly stirred for 3 hr. Toluene was concentrated and separated with the column (the ratio of ethyl acetate to n-hexane is 1 to 1). As a result, 7.7 g of 99.0% or more Simvastatin was obtained.

Example 4

Production of Simvastatin 120 ml of acetonitrile was added to the concentrated solution of 6(R)-[2-(8'(S)-(4-butyl-2,2-dimethyloxy)-2'(S), 6'(R)-dimethyl-1', 2', 6', 7', 8', 8'a(R)-hexahydronaphthyl-1' (S)ethyl-4(R)-t-butyldimethylsilyloxy-3,4,5,6-tetrahydro-2H-pyran-2-on. 7 ml of distilled water and 0.5 ml of methanesulfonic acid were added to the solution. This solution was stirred at 50 °C. for 3 hr. After stirring, 42 ml of 2N NaOH was added to the solution. 150 ml of Ethyl acetate and 150 ml of distilled water were added to the solution, stirred, and the aqueous layer was separated. The organic layer was separated by acidifying the aqueous layer mixed with 125 ml of ethyl acetate using hydrochloride. 42 ml of methanol and 3.5 ml of 28% ammonia water was added to the organic layer, which leads to crystalization. Crystals were filtered, washed with 20 ml of ethyl acetate/methanol(3.5/1) and 20 ml of toluene, sequentially. After washing, crystals were added to 150 ml of toluene. Toluene was concentrated and separated. The resulting solution was mixed with 150 ml of cyclohexane, and stirred. As a result, 6.6 g of crude Simvastatin was obtained. The crude Simvastatin was re-crystalized with ethanol/distilled water, and 6.2 g of 90.0% or more Simvastatin was obtained.

It is clear that the present invention is useful in industry because the higher yield of acylated substances (IV) is obtained without use of LiBr and separation of acylchloride (II).

What is claimed is:
1. A process for producing the compound of formula (I):

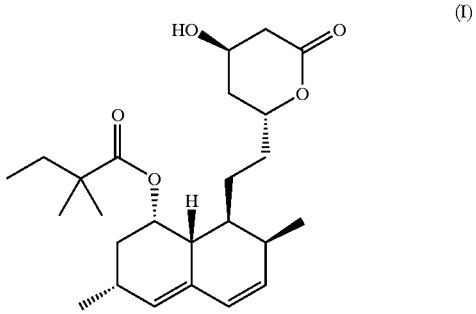

comprising the steps of reacting 6(R)-[2-(8'(S)-hydroxy-2'(S), 6'(R)-dimethyl-1', 2', 6', 7', 8', 8'a(R)-hexahydronaphthyl-1'(S)ethyl-4(R)-t-butyldimethylsilyloxy-3,4,5,6-tetrahydro-2H-pyran-2-on with the compound of formula (VI):

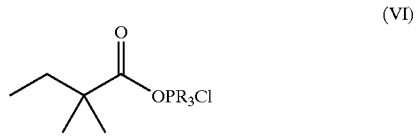

wherein R is methyl, ethyl, propyl, n-butyl, t-butyl, or phenyl, and;
hydroxylating the resulting compound of formula (IV):

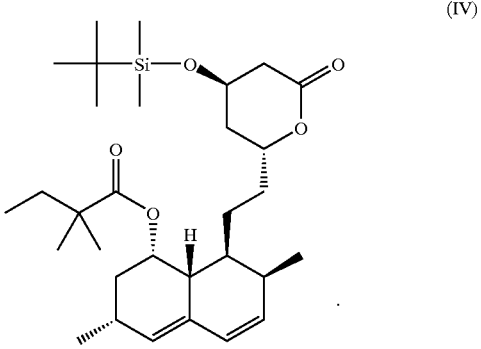

2. A process according to claim 1 wherein said compound of formula (VI) is produced by the reaction of halogenide, resulted from the reaction of formula (V):

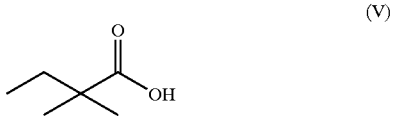

3. A process according to claim 2 wherein said trialkylphosphine is triphenylphosphine.
4. A process according to claim 2 wherein said halogen compound is hexachloroethane.
5. A process according to claim 2 wherein the amount of halogen compound is from 1.0 to 4.0 equivalent.
6. A process according to claim 1 wherein the organic solvent is dichloroethane.

* * * * *